United States Patent
Lai et al.

(10) Patent No.: US 9,310,299 B2
(45) Date of Patent: Apr. 12, 2016

(54) BIOCHIP DETECTING DEVICE AND LIGHT SOURCE DETECTING METHOD THEREOF

(71) Applicant: Wistron Corporation, New Taipei (TW)

(72) Inventors: Chun-Chih Lai, New Taipei (TW); Yi-Cheng Lee, New Taipei (TW); Ting-Wen Liu, New Taipei (TW)

(73) Assignee: Wistron Corporation, New Taipei (TW)

( * ) Notice: Subject to any disclaimer, the term of this patent is extended or adjusted under 35 U.S.C. 154(b) by 44 days.

(21) Appl. No.: 13/914,635

(22) Filed: Jun. 11, 2013

(65) Prior Publication Data

US 2014/0104610 A1    Apr. 17, 2014

(30) Foreign Application Priority Data

Oct. 17, 2012   (TW) .............................. 101138284 A

(51) Int. Cl.
   *G01N 21/25*   (2006.01)
   *G01N 21/63*   (2006.01)
(52) U.S. Cl.
   CPC .............. *G01N 21/63* (2013.01); *G01N 21/253* (2013.01)
(58) Field of Classification Search
   CPC . G01N 21/253; G01N 21/63; G01J 2001/161; G01J 2001/4247
   USPC .......... 356/402–425, 432–444, 218–234, 244
   See application file for complete search history.

(56) References Cited

U.S. PATENT DOCUMENTS

| | | | | |
|---|---|---|---|---|
| 4,223,995 A | * | 9/1980 | Fletcher | 356/418 |
| 6,128,085 A | * | 10/2000 | Buermann et al. | 356/369 |
| 7,095,500 B2 | * | 8/2006 | Banks | 356/417 |

(Continued)

FOREIGN PATENT DOCUMENTS

| | | |
|---|---|---|
| CN | 1198124 | 4/2005 |
| CN | 2862013 | 1/2007 |

(Continued)

OTHER PUBLICATIONS

"Office Action of Taiwan Counterpart Application", issued on Aug. 11, 2014, with English translation thereof, p. 1-p. 12.
"Office Action of China Counterpart Application", issued on Aug. 19, 2015, with English translation thereof, p. 1-p. 17.

*Primary Examiner* — Kara E Geisel
*Assistant Examiner* — Shawn Decenzo
(74) *Attorney, Agent, or Firm* — Jianq Chyun IP Office

(57) ABSTRACT

A biochip detecting device for detecting a biochip is provided. The biochip receives an incident light to produce an excitation light. Both the incident light and the excitation light include a specific wavelength. The biochip detecting device includes a light source producing the incident light, an optical attenuator, a filter, a sensor, and a control module electrically connected to the light source and the sensor. Light with the specific wavelength passes through the filter. The optical attenuator disposed between the light source and the filter attenuates an intensity of the incident light, and replaces the biochip. The sensor detects an intensity of the light with the specific wavelength attenuated by the optical attenuator, and generates an intensity signal. The control module adjusts the intensity of the incident light according to whether the intensity signal is complied with a predetermined requirement. A detection method for the light source is provided.

5 Claims, 4 Drawing Sheets

(56) References Cited

U.S. PATENT DOCUMENTS

| | | |
|---|---|---|
| 7,173,701 B2 * | 2/2007 | Wang et al. .................... 356/417 |
| 7,199,360 B1 * | 4/2007 | Montagu .................... 250/252.1 |
| 2007/0070345 A1 * | 3/2007 | Araragi et al. ................ 356/318 |
| 2011/0007055 A1 | 1/2011 | Wang |
| 2013/0003054 A1 * | 1/2013 | Kamimura .................... 356/300 |

FOREIGN PATENT DOCUMENTS

| | | |
|---|---|---|
| TW | I281947 | 6/2007 |
| TW | M339775 | 9/2008 |
| TW | 201007080 | 2/2010 |
| TW | 201140269 | 11/2011 |
| WO | 2011118309 | 9/2011 |

* cited by examiner

BIOCHIP DETECTING DEVICE AND LIGHT SOURCE DETECTING METHOD THEREOF

CROSS-REFERENCE TO RELATED APPLICATION

This application claims the priority benefit of Taiwan application serial no. 101138284, filed on Oct. 17, 2012. The entirety of the above-mentioned patent application is hereby incorporated by reference herein and made a part of this specification.

BACKGROUND

1. Technical Field

The invention relates to a detecting device and a detecting method. Particularly, the invention relates to a biochip detecting device and a light source detecting method thereof.

2. Related Art

Presently, types of biochip detecting devices are diversified, and a flow cytometer is one of the biochip detecting devices. The flow cytometer can categorize cells suspended in fluid, and can detect physical and chemical properties of the cells. When the flow cytometer is used to categorize the cells, the cells are selectively added with certain charges, and are deflected to outflow from different outlets after passing through an electric field. In this way, the cells in a mixture can be quickly and accurately categorized.

When the flow cytometer is used to detect physical and chemical properties of the cells, since the flow cytometer has a plurality of light sources and photo detectors, when the light irradiates each of the cells suspended in the fluid, the light is scattered to produce a scattered light, and the cell is probably excited to emit a fluorescence light with a frequency lower than that of an excitation light. The scattered light and the fluorescence light are recorded by the photo detectors, and the physical and chemical properties of the cells can be deduced according to detection results of the photo detectors.

Since the biochip detecting device has a high requirement on the excitation light source, once the property of the light source attenuates, it may influence correctness of the detection result. Moreover, when the light source is required to be replaced, a user may need to open the biochip detecting device to disassemble an internal excitation light source element, so as to replace the light source. Even, the user may need to use a specific light source element detector to detect the light source. Therefore, regarding the present biochip detecting device, a simple and effective detecting method is required to detect an attenuation degree of the light source, so as to facilitate the user operating the biochip detecting device.

SUMMARY

The invention is directed to a biochip detecting device, which is capable of self-detecting an attenuation degree of a light source and self-compensating an intensity of the light source.

The invention is directed to a light source detecting method for a biochip detecting device, by which the biochip detecting device is capable of self-detecting an attenuation degree of a light source and self-compensating an intensity of the light source.

The invention provides a biochip detecting device, which is used to detect a biochip, wherein the biochip is adapted to receive an incident light to produce an excitation light. Both of the incident light and the excitation light contain a specific wavelength. The biochip detecting device includes a light source, an optical attenuator, a filter, a sensor, and a control module. The light source produces the incident light. The filter filters light with a wavelength other than the specific wavelength. The optical attenuator is removably disposed between the light source and the filter to attenuate an intensity of the incident light, and used to replace the biochip. The sensor detects an intensity of the light with the specific wavelength attenuated by the optical attenuator, and generates an intensity signal correspondingly. The control module is electrically connected to the sensor and the light source, and determines whether the intensity signal generated by the sensor complies with a predetermined requirement, so as to correspondingly adjust the intensity of the incident light.

The invention provides a light source detecting method for a biochip detecting device, where the biochip detecting device is used to detect a biochip, and the biochip is adapted to receive an incident light to produce an excitation light. Both of the incident light and the excitation light contain a specific wavelength. The biochip detecting device includes a light source, a filter, a sensor, and a control module. The light source produces the incident light, and the control module is electrically connected to the sensor and the light source. The light source detecting method includes following steps. An optical attenuator is disposed between the light source and the filter to replace the biochip and attenuate an intensity of the incident light. The light source is driven to produce the incident light, and the incident light sequentially passing through the optical attenuator and the filter and is received by the sensor, and the sensor generates a first sensing voltage corresponding to the intensity of the received light. The control module obtains the first sensing voltage, and determines whether the first sensing voltage complies with a predetermined requirement, so as to correspondingly adjust the intensity of the incident light.

In an embodiment of the invention, the biochip detecting device further includes a lens, where the incident light is transmitted to the optical attenuator or the biochip through the lens.

In an embodiment of the invention, the control module further includes a signal processing unit and a control unit. The signal processing unit is electrically connected to the sensor to receive and adjust the intensity signal transmitted by the sensor. The control unit is electrically connected to the signal processing unit and the light source. The control unit determines whether the adjusted intensity signal transmitted from the signal processing unit complies with the predetermined requirement, so as to correspondingly adjust a driving voltage of the light source.

In an embodiment of the invention, the optical attenuator attenuates an intensity of the light with the specific wavelength.

In an embodiment of the invention, the light source detecting method for the biochip detecting device further includes following steps. The light source is driven by a predetermined driving voltage, and the control module obtains a predetermined sensing voltage. The light source is driven by a first driving voltage, and the control module obtains the first sensing voltage. The first sensing voltage and the predetermined sensing voltage are compared to generate a difference ratio (Z), where $Z=a*(Y/X)$, Y is the first sensing voltage, X is the predetermined sensing voltage, and a is a constant. When the difference ratio (Z) is smaller than a predetermined value, the control module drives the light source through a second driving voltage, and the control module obtains a second sensing voltage, where the second driving voltage is greater than the first driving voltage, and the second sensing voltage is greater than the first sensing voltage.

In an embodiment of the invention, the first sensing voltage is smaller than a saturation voltage of the sensor.

In an embodiment of the invention, the control module has a signal processing unit, and the first sensing voltage is smaller than a readable voltage of the signal processing unit.

In an embodiment of the invention, the light source detecting method for the biochip detecting device further includes driving the light source through a third driving voltage to produce another incident light, and transmitting the other incident light to the sensor through the filter, so that the sensor generates a third sensing voltage for transmitting to the control module, where the filter filters light with a wavelength other than the specific wavelength, the third sensing voltage is smaller than a saturation voltage of the sensor, and the third driving voltage is smaller than the first driving voltage.

In an embodiment of the invention, the control module has a signal processing unit, and the third sensing voltage is smaller than a readable voltage of the signal processing unit.

According to the above descriptions, the biochip detecting device of the present invention uses the optical attenuator removably disposed between the light source and the filter to implement self-detection of the light source intensity. When the user needs to detect an attenuation degree of the light source in the biochip detection device, the user disposes the optical attenuator between the light source and the filter to replace the biochip, where the optical attenuator attenuates the intensity of the incident light generated by the light source such that the intensity of the light source is adapted to be sensed by the sensor. During the process of detecting the attenuation degree of the light source, the biochip detecting device uses the control module disposed in internal of the biochip detecting device to determine a magnitude of the intensity of the incident light generated by the light source, and uses the control module to adjust the intensity of the incident light. In the whole detecting flow of the attenuation degree of the light source, light source detection and light intensity compensation can be achieved without using an extra detection device, which is convenient for the user to operate the biochip detection device of the invention.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION OF DISCLOSED EMBODIMENTS

Figure 1:
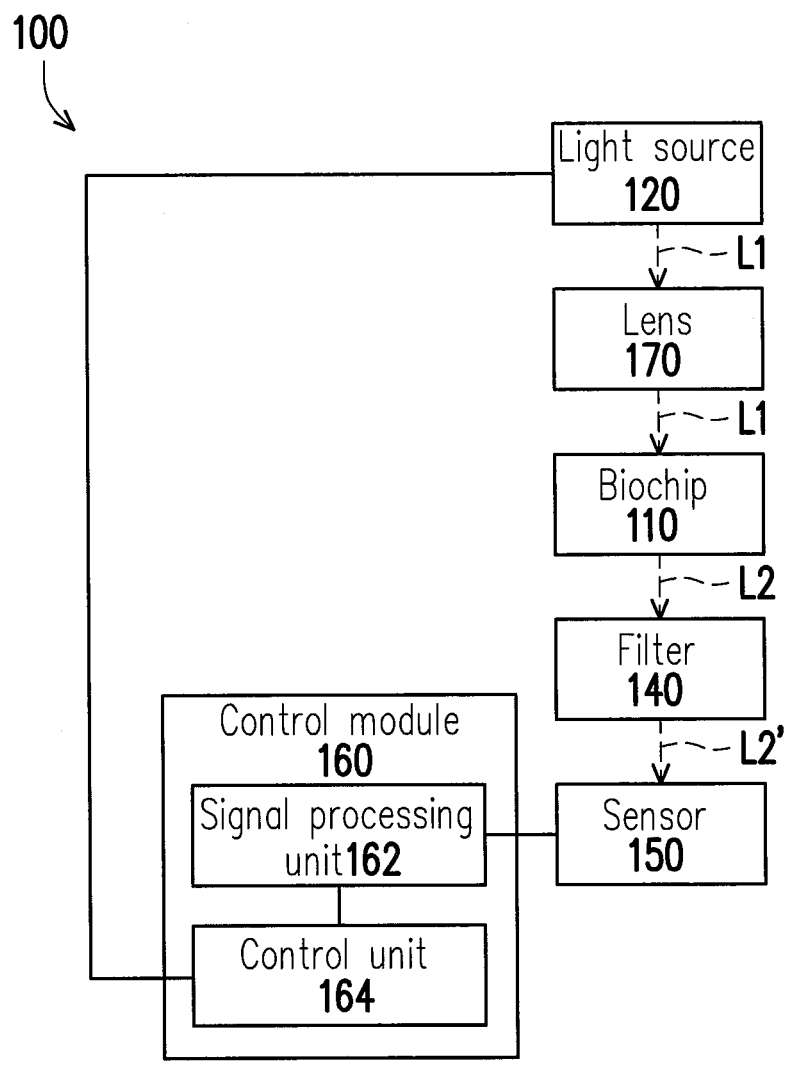
FIG. 1 is a schematic diagram of a biochip detecting device according to an embodiment of the invention.

FIG. 1 is a schematic diagram of a biochip detecting device according to an embodiment of the invention. Referring to FIG. 1, the biochip detecting device 100 is, for example, a flow cytometer used in a biomedical detection field for detecting a biochip 110. The biochip 110 is adapted to receive an incident light L1 to produce an excitation light L2, where both of the incident light L1 and the excitation light L2 contain a specific wavelength.

In the present embodiment, the biochip detecting device 100 includes a light source 120, a lens 170, a filter 140, a sensor 150 and a control module 160. The light source 120 is, for example, a laser or a light-emitting diode, which is used to produce the incident light L1. The lens 170 is, for example, a collimator, which is used to focus the incident light L1 on the biochip 110. The filter 140 is, for example, a band pass filter, which filters light with a wavelength other than a specific wavelength, and converts the light with the wavelength other than the specific wavelength into heat or other manner. The biochip 110 is removably disposed between the light source 120 and the filter 140. The control module 160 is electrically connected to the sensor 150 and the light source 120, and receives and determines an electronic signal produced and transmitted by the sensor 150 after the sensor 150 receives the light to serve as a basis for controlling the property of the light source 120. Here, a type of the light source 120, the lens 170 or the filter 140 is not limited by the invention, which can all be applied in the present embodiment as long as it is complied with a detection requirement of the biochip detecting device 100.

In this way, the incident light L1 emitted from the light source 120 is incident to the biochip 110 through the lens 170, and the biochip 110 receives the incident light L1 to generate the excitation light L2. Then, the excitation light L2 passes through the filter 140 to form an excitation light L2' with the specific wavelength (i.e. the lights with the other wavelengths are filtered), and the sensor 150 senses the excitation light L2'. The control module 160 receives and determines the electronic signal (for example, a sensing voltage generated by the sensor 150 after the sensor 150 receives the excitation light L2') transmitted from the sensor 150, so as to detect physical and chemical properties of an object to be tested in the biochip 110.

Figure 2:
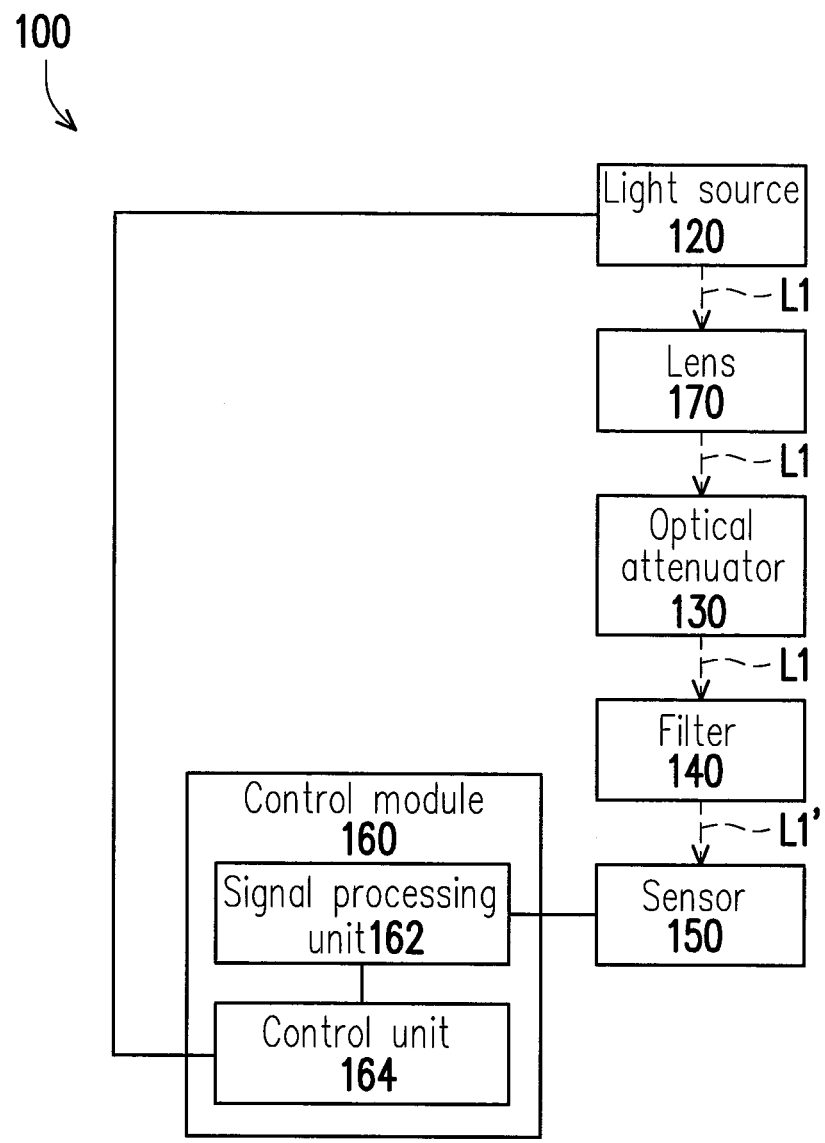
FIG. 2 is a schematic diagram of the biochip detecting device of FIG. 1 that performs light source detection.

FIG. 2 is a schematic diagram of the biochip detecting device of FIG. 1 that performs light source detection. Referring to FIG. 2 and FIG. 1, since the physical and chemical properties of the object to be tested in the biochip 110 are obtained according to the excitation light L2 produced by the biochip 110 after receiving the incident light L1, the attenuation degree of the light source 120 is very important for the biochip detecting device 100. In order to achieve an effect that the biochip detection device 100 detects the attenuation degree of the light source 120 through a more convenient means, in the present embodiment, an optical attenuator 130 is disposed between the light source 120 and the filter 140 to detect the attenuation degree of the light source 120. Namely, when the user places the biochip 110 between the light source 120 and the filter 140 of the biochip detecting device 100, the biochip detecting device 100 can be used to perform a general biomedical detection, and when the user places the optical attenuator 130 between the light source 120 and the filter 140 to replace the biochip 110, the biochip detecting device 100 can self-detect the light source 120.

Referring to FIG. 2, the biochip detecting device 100 further includes the optical attenuator 130, which is removably disposed between the light source 120 and the filter 140, i.e. the optical attenuator 130 is disposed at a position where the biochip 110 of FIG. 1 locates to replace the biochip 110. Here, the optical attenuator 130 can be a neutral density filter (ND filter) used for decreasing a light intensity, though the invention is not limited thereto.

In detail, if the user places the optical attenuator 130 between the light source 120 and the filter 140, when the light source 120 of the biochip detecting device 100 is driven to emit the incident light L1, as the incident light L1 does not pass through the biochip 110, the light intensity of the incident light L1 is strong, which may even cause oversaturation of the sensor 150, so that the optical attenuator 130 is used to decrease the light intensity. In other words, in the biochip detecting device 100, the sensor 150 is designed to detect the excitation light L2 generated by the biochip 110 after receiving the incident light L1, so that the energy that can be received by the sensor 150 is adapted to the energy of the excitation light L2, and the energy of the excitation light L2 is generally far less than that of the incident light L1. Therefore, in the present embodiment, the optical attenuator 130 is used to attenuate the energy of the incident light L1, so that the energy of the incident light L1 passing through the optical attenuator 130 is decreased, which is suitable to be detected by the sensor 150.

In this way, the incident light L1' formed by the incident light L1 sequentially passing through the lens 170, the optical attenuator 130 and the filter 140 can be received by the sensor 150. In the above process, the optical attenuator 130 is used to attenuate the intensity of the incident light L1, i.e. to decrease the incident light L1 containing any wavelength, and the filter 140 filters light with the wavelength other than the above specific wavelength.

Then, the control module 160 adjusts the intensity of the incident light L1 according to an intensity of the light with the specific wavelength that is sensed by the sensor 150, namely, the control module 160 determines whether an intensity signal generated by the sensor 150 after the sensor 150 receives the incident light L1' complies with a predetermined requirement, and correspondingly adjusts the intensity of the incident light L1. For example, when the intensity of the incident light L1' is too small, the control module 160 can adjust the intensity of the incident light L1 to increase the intensity thereof, so as to achieve effects of self-detection and self-compensation.

An advantage of using the biochip detecting device 100 of the present embodiment is that when the user needs to detect the attenuation degree of the light source 120, the optical attenuator 130 is disposed between the light source 120 and the filter 140 to replace the biochip 110 without using an extra detector to detect the attenuation degree of the light source 120 or removing the light source 120 from the device. Meanwhile, the control module 160 in internal of the biochip detecting device 100 can directly determine and adjust the intensity of the incident light L1.

Referring to FIG. 2 and FIG. 1, the control module 160 includes a signal processing unit 162 and a control unit 164 electrically connected to each other, wherein the signal processing unit 162 is electrically connected to the sensor 150 to receive and adjust the intensity signal transmitted from the sensor 150, for example, amplifies the intensity signal transmitted from the sensor 150 by a suitable ratio to a magnitude that can be read by the control module 160. The control unit 164 is electrically connected to the light source 120, and determines the adjusted intensity signal transmitted from the signal processing unit 162 to adjust the driving voltage of the light source 120.

In this way, during the process of detecting the light source 120 shown in FIG. 2, after the incident light L1 that is attenuated by the optical attenuator 130 is transmitted to the sensor 150, the signal processing unit 162 can decrease a ratio of the amplified signal thereof, so that it is adapted to be received by the control unit 164.

Figure 3:
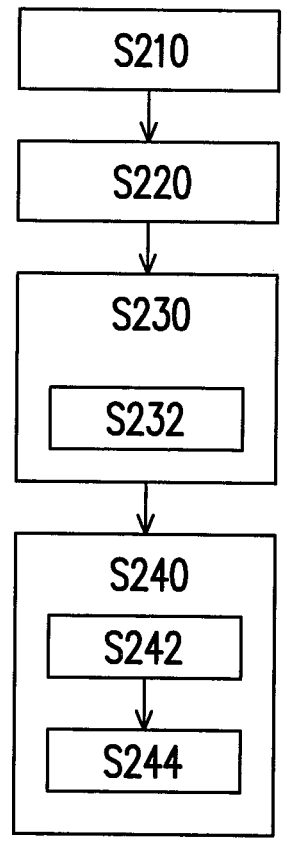
FIG. 3 is a flowchart illustrating a light source detecting method for a biochip detecting device according to an embodiment of the invention.

FIG. 3 is a flowchart illustrating a light source detecting method for a biochip detecting device according to an embodiment of the invention.

Referring to FIG. 2 and FIG. 3, in step S220, the optical attenuator 130 is disposed between the light source 120 and the filter 140 to replace the biochip 110.

In step S230, the light source 120 is driven to produce the incident light L1, and the incident light L1 sequentially passes through the optical attenuator 130 and the filter 140 to form the incident light L1', and the incident light L1' is transmitted to the sensor 150, and the sensor 150 accordingly generates a first sensing voltage. Now, the first sensing voltage generated by the sensor 150 in response to the incident light L1 is smaller than the saturation voltage of the sensor 150.

In step S240, the control module 160 obtains the first sensing voltage, and adjusts the intensity of the incident light L1 according to the first sensing voltage. Here, the first sensing voltage is smaller than a readable voltage of the signal processing unit 162, so as to avoid a situation that the signal processing unit 162 cannot read the value of the first sensing voltage.

Referring to FIG. 3, in detail, in the step S210, the light source 120 is driven by a predetermined driving voltage, and the control module 160 obtains a predetermined sensing voltage X corresponding to the predetermined driving voltage. For example, such step is suitable for product tuning after the biochip detecting device 100 is fabricated Then, the factory predetermined sensing voltage X can be compared with the first sensing voltage obtained when the user operates the biochip detecting device 100. Then, in step S232, the user drives the light source 120 by the first driving voltage, and now the control module 160 obtains a first sensing voltage Y corresponding to the first driving voltage.

Then, in step S242, the control module 160 of the biochip detecting device 100 compares a difference between the first sensing voltage Y and the predetermined sensing voltage X to generate a difference ratio (Z), where $Z=a*(Y/X)$, Y is the first sensing voltage, X is the predetermined sensing voltage, and a is a constant, and the value of the constant a is varied along with the type of the light source 120.

Then, in step S244, when the difference ratio (Z) is smaller than a predetermined value, the control module 160 drives the light source 120 by a second driving voltage, and the control module 160 obtains a second sensing voltage, where the second driving voltage is greater than the first driving voltage, and the second sensing voltage is greater than the first sensing voltage. In such step, the difference ratio (Z) can serve as a comparison reference, according which the control module 160 determines whether or not to adjust the intensity of the incident light L1. Moreover, the user can determine the predetermined value according to a usage environment or a device characteristic.

In other words, the difference ratio (Z) is a comparison reference in the biochip detecting device 100, according which the control module 160 determines whether or not to self-compensate the intensity of the light source 120. When the difference ratio (Z) is smaller than the predetermined value, it represents that the intensity of the incident light L1 is smaller than a predetermined value, and the control module 160 drives the light source 120 by a second driving voltage greater than the first driving voltage, such that the intensity of the incident light L1 generated by the light source 120 can be increased to make the difference ratio (Z) reaching the predetermined value. After comparison of the difference ratio (Z) is completed, the detection flow of the light source 120 of the whole biochip detecting device 100 is completed. Moreover, although it is not illustrated in the flowchart of FIG. 2, when the attenuation degree of the light source 120 reaches a certain degree (for example, when the driving voltage is increased to a predetermined maximum value though the difference ratio (Z) still cannot reach the predetermined value), the control module 160 can provide a prompt message to the user to remind the user to replace the light source 120.

Figure 4:
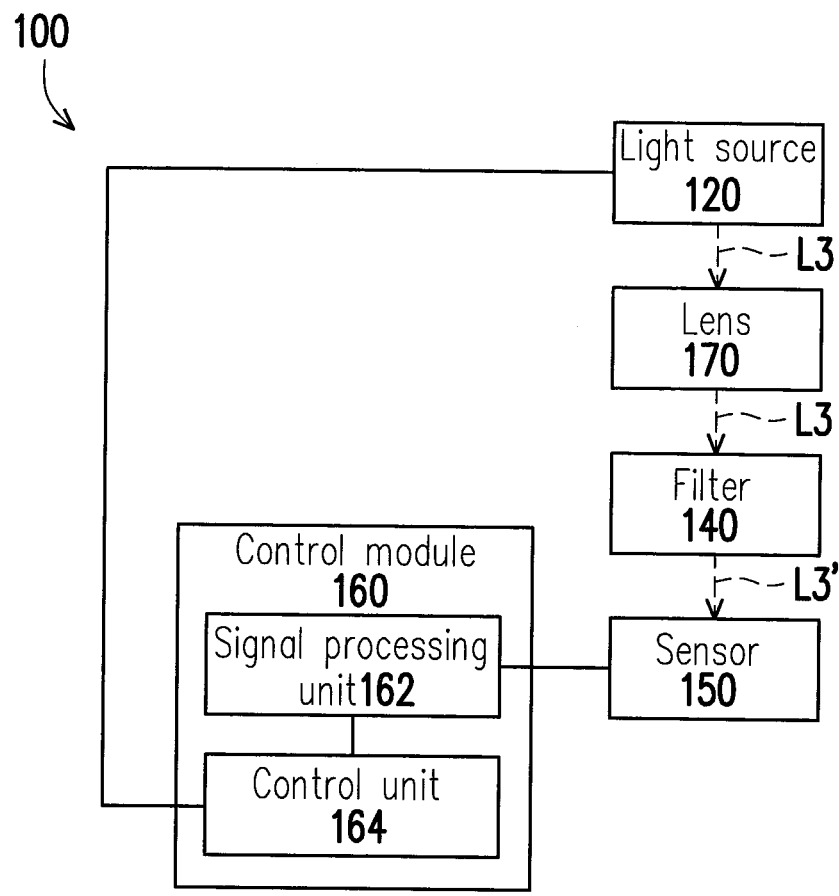
FIG. 4 is a schematic diagram of the biochip detecting device of FIG. 1 that performs initial light source detection.

FIG. 4 is a schematic diagram of the biochip detecting device of FIG. 1 that performs initial light source detection. Referring to FIG. 4, on the other hand, before the user configures the optical attenuator 130, a following step is performed to implement an initial detection on the light source 120:

A third driving voltage is used to drive the light source 120 to produce an incident light L3, and the incident light L3 directly passes through the filter 140 and is transmitted to the sensor 150, and the sensor 150 accordingly generates a third sensing voltage. The same to the aforementioned embodiment, the filter 140 is used to filter the light with a wavelength other than the specific wavelength, and the third sensing voltage is smaller than the saturation voltage of the sensor 150.

It should be noticed that the light source 120 is driven by the third driving voltage that is far less than the first driving voltage, such that the incident light L3 can be received by the sensor without additional light intensity attenuation. In other words, the third sensing voltage is smaller than the saturation voltage of the sensor 150, and is also smaller than the readable voltage of the signal processing unit 162. Such step is to preliminarily determine the attenuation degree of the light source 120 to facilitate the user determining whether or not to further adjust the intensity of the light source 120.

Though the above step is not limited to be executed before the step S220, and the user can regularly execute the above step according to a maintenance requirement of the device.

In summary, the biochip detecting device of the present invention achieves a self-detection effect and a self-compensation effect of the light source by using the optical attenuator and the related members of the biochip detecting device. In this way, the biochip detecting device may achieve the same effect without using an extra detecting device or disassembling the light source, so that the biochip detection device of the invention has a better operation convenience.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims and their equivalents.

What is claimed is:

1. A light source detecting method for a biochip detecting device, wherein the biochip detecting device is used to detect a biochip, and the biochip is adapted to receive a single incident light to produce an excitation light, both of the single incident light and the excitation light contain a specific wavelength, the biochip detecting device comprises a light source for generating the single incident light, a filter, a sensor, and a control module, and the control module is electrically connected to the sensor and the light source, wherein the light source, the single incident light, the biochip, the excitation light, and the sensor form a single optical path, the light source detecting method comprising:

disposing a single optical attenuator on the single optical path and between the light source and the filter to replace the biochip and attenuate an intensity of the single incident light, wherein the single optical attenuator has a attenuation degree as the biochip to attenuate the intensity of the single incident light so as to replace the biochip under detection, and;

driving the light source to produce the single incident light, and making the single incident light to sequentially pass through the single optical attenuator and the filter for being received by the sensor, such that the sensor generates a first sensing voltage corresponding to the intensity of the received light;

obtaining the first sensing voltage by the control module, and determining whether the first sensing voltage complies with a predetermined requirement, so as to correspondingly adjust the intensity of the single incident light on the single optical path; and before disposing the single optical attenuator, driving the light source through a third driving voltage to produce another single incident light, and transmitting the other single incident light to the sensor through the filter, so that the sensor generates a third sensing voltage for transmitting to the control module, wherein the filter filters light with a wavelength other than the specific wavelength, the third sensing voltage is smaller than a saturation voltage of the sensor, the third driving voltage is smaller than a first driving voltage, and an initial detection on the light source has been implemented.

2. The light source detecting method for the biochip detecting device as claimed in claim 1, further comprising:

driving the light source by a predetermined driving voltage, and the control module obtaining a predetermined sensing voltage;

driving the light source by the first driving voltage, and the control module obtaining the first sensing voltage;

comparing the first sensing voltage and the predetermined sensing voltage to generate a difference ratio (Z), wherein Z=a*(Y/X), Y is the first sensing voltage, X is the predetermined sensing voltage, and a is a constant; and when the difference ratio (Z) is smaller than a predetermined value, the control module driving the light source by a second driving voltage and the control module obtaining a second sensing voltage, wherein the second driving voltage is greater than the first driving voltage, and the second sensing voltage is greater than the first sensing voltage.

3. The light source detecting method for the biochip detecting device as claimed in claim 1, wherein the first sensing voltage is smaller than a saturation voltage of the sensor.

4. The light source detecting method for the biochip detecting device as claimed in claim 1, wherein the control module has a signal processing unit, and the first sensing voltage is smaller than a readable voltage of the signal processing unit.

5. The light source detecting method for the biochip detecting device as claimed in claim 1, wherein the control module has a signal processing unit, and the third sensing voltage is smaller than a readable voltage of the signal processing unit.

* * * * *